United States Patent [19]
Trauthen et al.

[11] Patent Number: 6,149,574
[45] Date of Patent: Nov. 21, 2000

[54] DUAL CATHETER RADIATION DELIVERY SYSTEM

[75] Inventors: Brett Trauthen, Newport Beach; Paul McCormick, Laguna Niguel; Maurice Buchbinder, La Jolla; Michael Henson, Trabuco Canyon, all of Calif.

[73] Assignee: Radiance Medical Systems, Inc., Irvine, Calif.

[21] Appl. No.: 09/040,172

[22] Filed: Mar. 17, 1998

Related U.S. Application Data

[63] Continuation-in-part of application No. 08/994,919, Dec. 19, 1997.

[51] Int. Cl.[7] ........................................... A61N 5/00
[52] U.S. Cl. ................................................... 600/3
[58] Field of Search .................................. 600/1, 3, 6, 7; 604/93, 96

[56] References Cited

U.S. PATENT DOCUMENTS

| | | |
|---|---|---|
| 3,324,847 | 6/1967 | Zoumboulis . |
| 4,115,536 | 9/1978 | Rothman et al. . |
| 4,124,705 | 11/1978 | Rothman et al. . |
| 4,126,669 | 11/1978 | Rothman et al. . |
| 4,225,790 | 9/1980 | Parsons, Jr. et al. . |
| 4,423,725 | 1/1984 | Baran et al. . |
| 4,581,017 | 4/1986 | Sahota . |
| 4,588,395 | 5/1986 | Lemelson . |
| 4,655,771 | 4/1987 | Wallsten . |
| 4,674,480 | 6/1987 | Lemelson . |
| 4,706,652 | 11/1987 | Horowitz . |
| 4,762,129 | 8/1988 | Bonzel . |
| 4,815,449 | 3/1989 | Horowitz . |
| 4,819,618 | 4/1989 | Liprie . |
| 4,878,492 | 11/1989 | Sinofsky et al. . |
| 5,011,677 | 4/1991 | Day et al. . |
| 5,019,369 | 5/1991 | Presant et al. . |
| 5,040,548 | 8/1991 | Yock . |

(List continued on next page.)

FOREIGN PATENT DOCUMENTS

| | | |
|---|---|---|
| WO 93/04735 | 3/1993 | WIPO . |
| WO 94/23789 | 10/1994 | WIPO . |
| WO 95/19807 | 7/1995 | WIPO . |
| WO 95/29008 | 11/1995 | WIPO . |
| WO 96/10436 | 4/1996 | WIPO . |
| WO 96/13303 | 5/1996 | WIPO . |
| WO 96/14898 | 5/1996 | WIPO . |
| WO 96/22121 | 7/1996 | WIPO . |
| WO 97/18012 | 5/1997 | WIPO . |

OTHER PUBLICATIONS

*Radiation Quantities and Units,* ICRU Report 33. International Commission on Radiation, Units and Measurements, Apr. 15, 1980.

(List continued on next page.)

*Primary Examiner*—Linda C. M. Dvorak
*Assistant Examiner*—R. Kearney
*Attorney, Agent, or Firm*—Knobbe, Martens, Olson & Bear, LLP.

[57] ABSTRACT

Disclosed is a dual catheter radiation delivery system, for delivering a dose of radiation to a treatment site, typically in a body lumen. The system comprises an outer sheath catheter, having an inflatable balloon thereon. The system further comprises an inner radiation delivery catheter, having a radially expandable structure such as a balloon with a radiation source thereon. The sheath catheter is positioned such that the sheath balloon is at the treatment site, and the radiation delivery catheter is translumaly advanced through the sheath catheter such that the radiation source is positioned within the sheath balloon. The radiation delivery balloon is inflated within the sheath balloon, to position the radioactive source near the vessel wall. The source may comprise a thin film carried by the radiation delivery balloon, having a radioactive isotope implanted therein or chemically bonded thereto. Alternatively, the radioactive isotope may be implanted within or adhered to the radiation delivery balloon.

9 Claims, 6 Drawing Sheets

U.S. PATENT DOCUMENTS

| | | |
|---|---|---|
| 5,059,166 | 10/1991 | Fischell et al. . |
| 5,061,273 | 10/1991 | Yock . |
| 5,106,360 | 4/1992 | Ishiwara et al. . |
| 5,176,617 | 1/1993 | Fischell et al. . |
| 5,199,939 | 4/1993 | Dake et al. . |
| 5,213,561 | 5/1993 | Weinstein et al. . |
| 5,267,960 | 12/1993 | Hayman et al. . |
| 5,302,168 | 4/1994 | Hess . |
| 5,302,369 | 4/1994 | Day et al. . |
| 5,354,257 | 10/1994 | Roubin et al. . |
| 5,411,466 | 5/1995 | Hess . |
| 5,424,288 | 6/1995 | Order . |
| 5,484,384 | 1/1996 | Fearnot ........................................ 600/3 |
| 5,498,227 | 3/1996 | Mawad . |
| 5,503,613 | 4/1996 | Weinberger . |
| 5,540,659 | 7/1996 | Tierstein . |
| 5,605,530 | 2/1997 | Fischell et al. . |
| 5,616,114 | 4/1997 | Thornton et al. . |
| 5,618,266 | 4/1997 | Liprie . |
| 5,643,171 | 7/1997 | Bradshaw et al. . |
| 5,653,683 | 8/1997 | D'Andrea . |
| 5,662,580 | 9/1997 | Bradshaw et al. . |
| 5,674,177 | 10/1997 | Hehrlein et al. . |
| 5,683,345 | 11/1997 | Waksman et al. . |
| 5,688,220 | 11/1997 | Verin et al. . |
| 5,707,332 | 1/1998 | Weinberger . |
| 5,713,828 | 2/1998 | Coniglione . |
| 5,720,717 | 2/1998 | D'Andrea . |
| 5,722,984 | 3/1998 | Fischell et al. . |
| 5,728,042 | 3/1998 | Schwager . |
| 5,730,698 | 3/1998 | Fischell et al. . |
| 5,755,690 | 5/1998 | Saab . |
| 5,762,631 | 6/1998 | Klein . |
| 5,782,740 | 7/1998 | Schneiderman . |
| 5,782,741 | 7/1998 | Bradshaw et al. . |
| 5,782,742 | 7/1998 | Crocker et al. . |
| 5,795,286 | 8/1998 | Fischell et al. . |
| 5,863,284 | 1/1999 | Klein ........................................ 600/3 |
| 5,871,436 | 2/1999 | Eury . |
| 5,879,282 | 3/1999 | Fischell et al. . |

OTHER PUBLICATIONS

Effects of high–dose intracoronary irradiation on vasomotor function and smooth muscle histopathology, Joseph G. Wiedermann, Jeffrey A. Leavy, Howard Amols, Allan Schwartz, Shunichi Homma, Charles Marboe and Judah Weinberger, Interventional Cardiology Center, Department of Medicine and Radiation Oncology and Section of Cardiac Pathology, Columbia–Presbyterian Medical Center and Columbia University, 1994 the American Physiological Society.

Intracoronary Irradiation Markedly Reduces Restenosis After Balloon Angioplasty in a Porcine Model, Joseph G. Wiedermann, MD, Charles Marboe, MD, Howard Amols, PhD, Allan Schwartz, MD, FACC, Judah Weinberger, MD, PhD, FACC, JACC vol. 23. No. 6, May 1994:1491–8.

Intracoronary Irradiation Markedly Reduces Neointimal Proliferation After Balloon Angioplasty in a Swine: Persistent Benefit at 6–Month Follow–up, Joseph G. Wiedermann, MD, Charles Marboe, MD, Howard Amols, PhD, Allan Schwartz, MD, JACC, Judah Weinberger, MD, PhD, JACC vol. 25. No. 6, May 1995:1451–6.

*Discoveries in Radiation for Restenosis,* Emory University of School of Medicine, Presented by The Andreas Gruentzig Cardiovascular Center and the Department of Radiation Oncology of Emory University School of Medicine, J.W. Mariott Hotel at Lenox, Atlanta, GA, Jan. 11–12, 1996.

Radioactive Balloon Catheter to Inhibit Restenosis after Angioplasty.

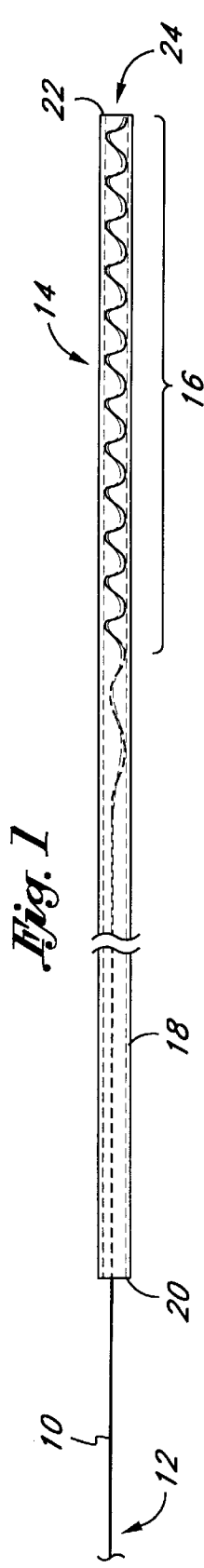
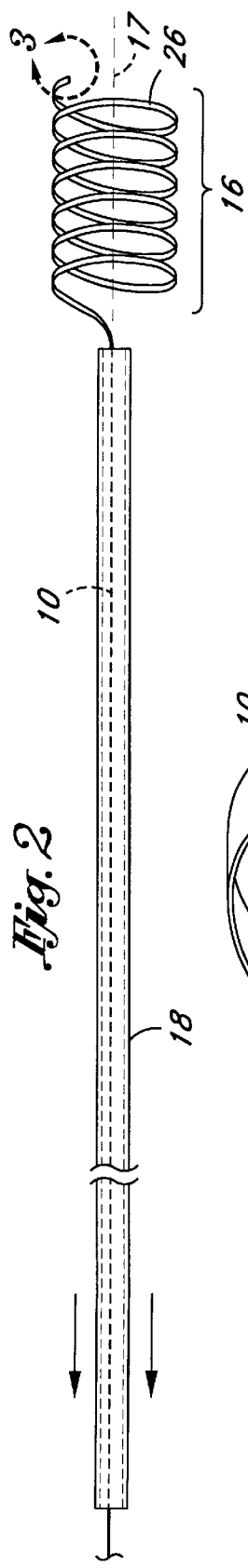
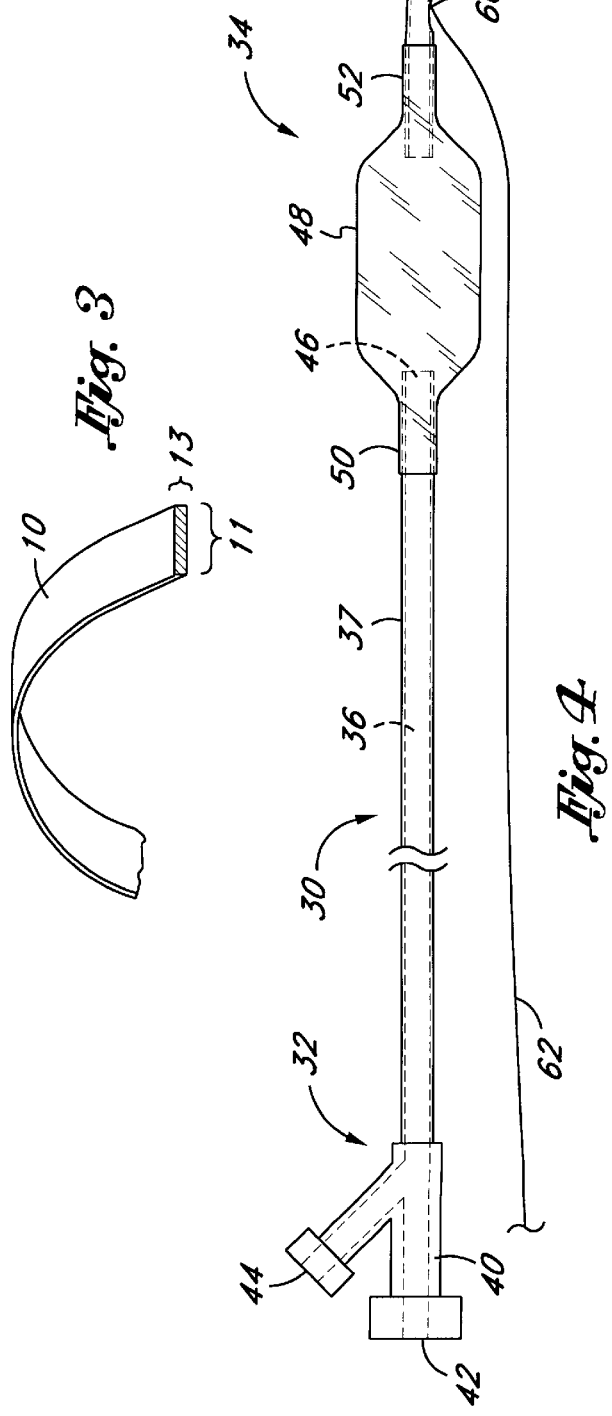

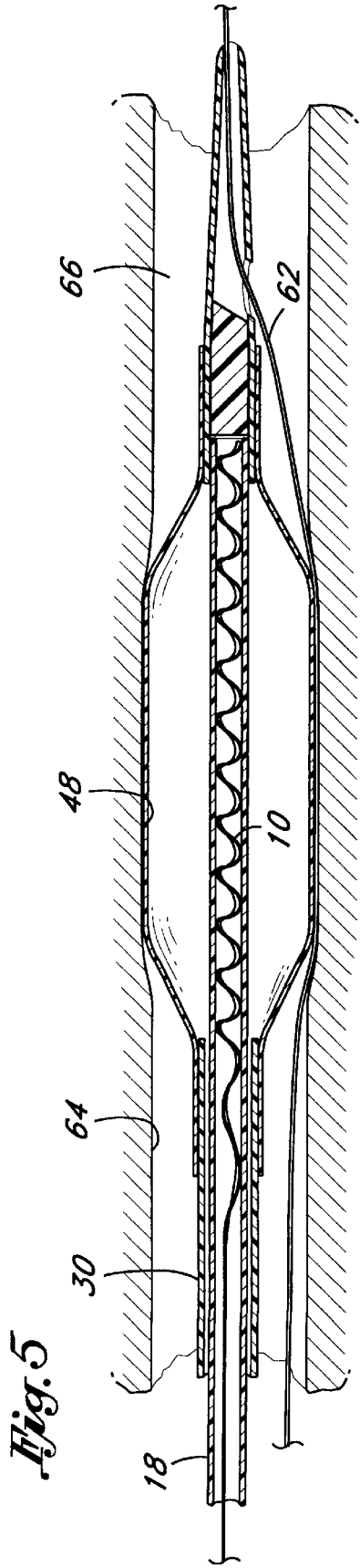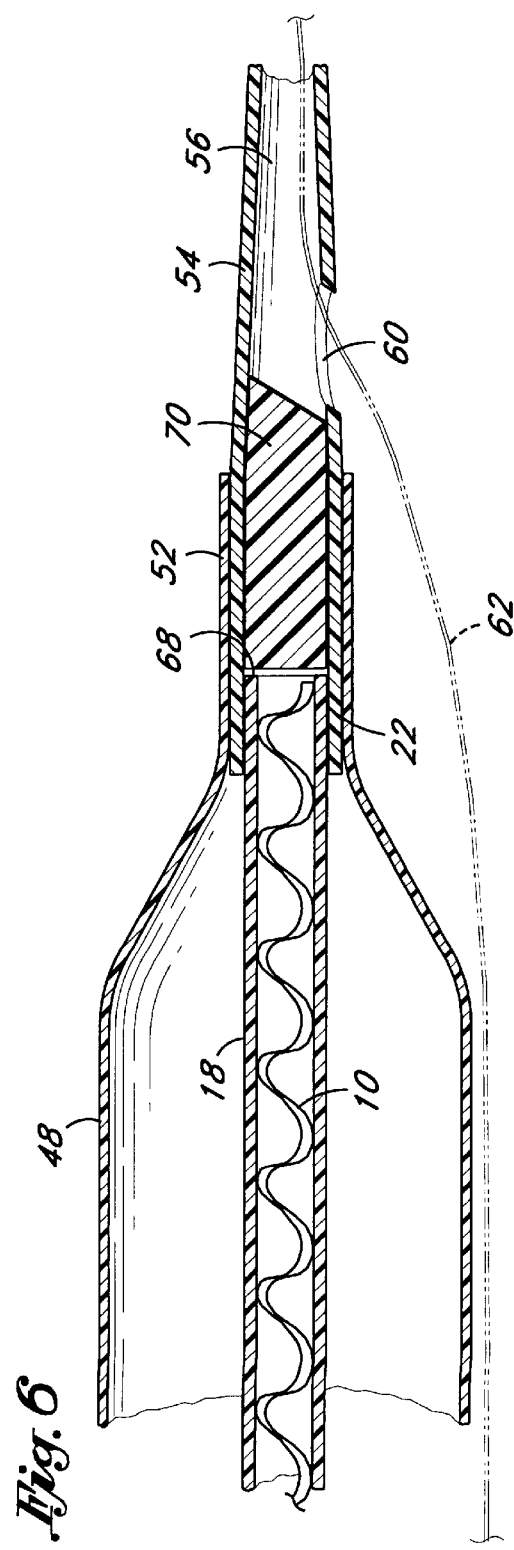

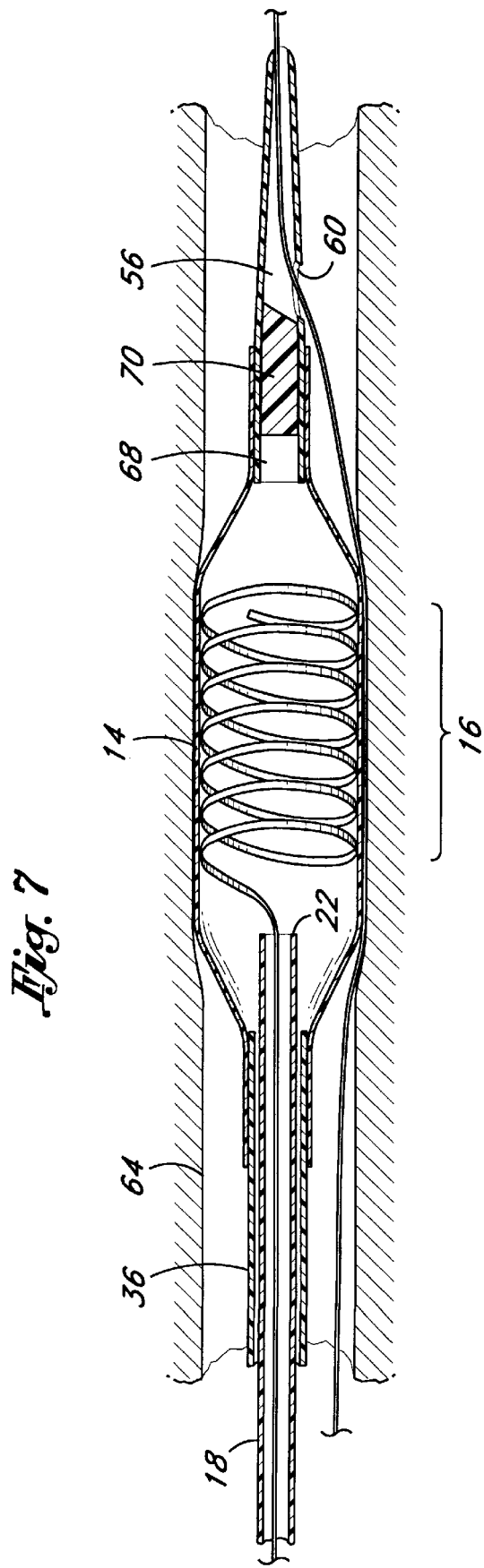

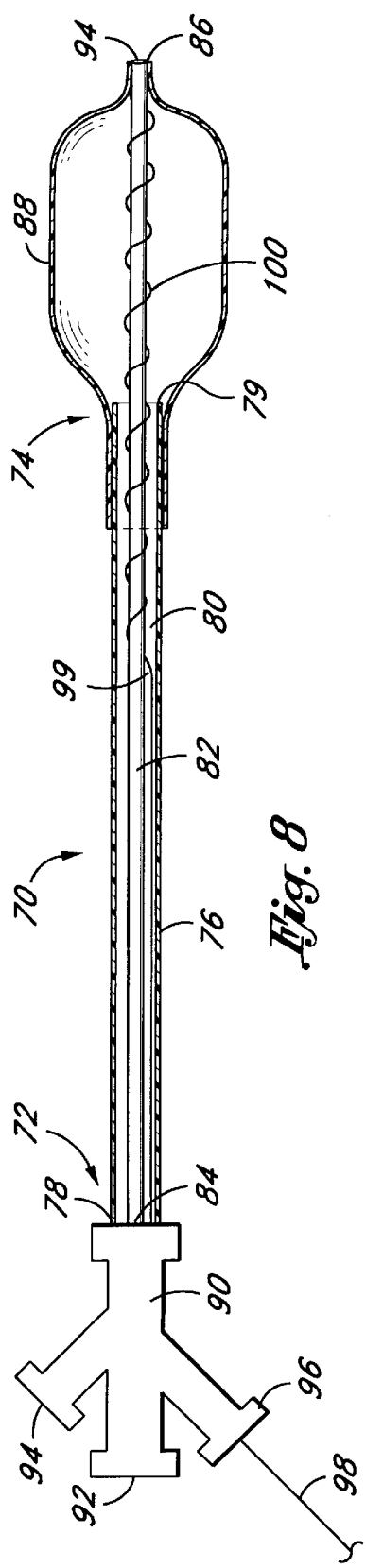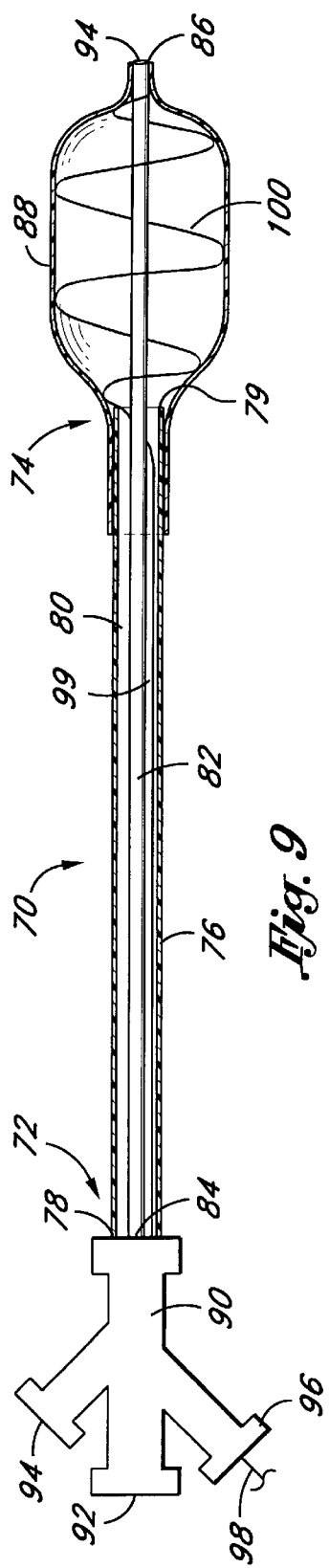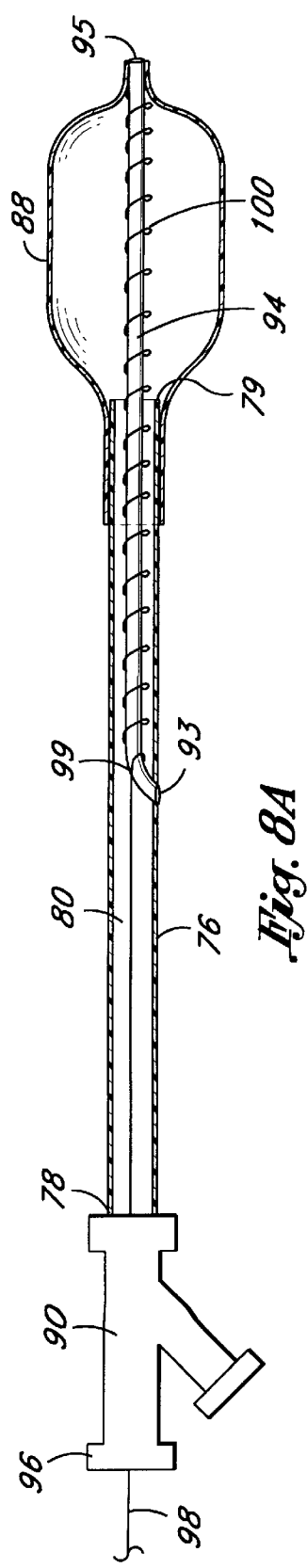

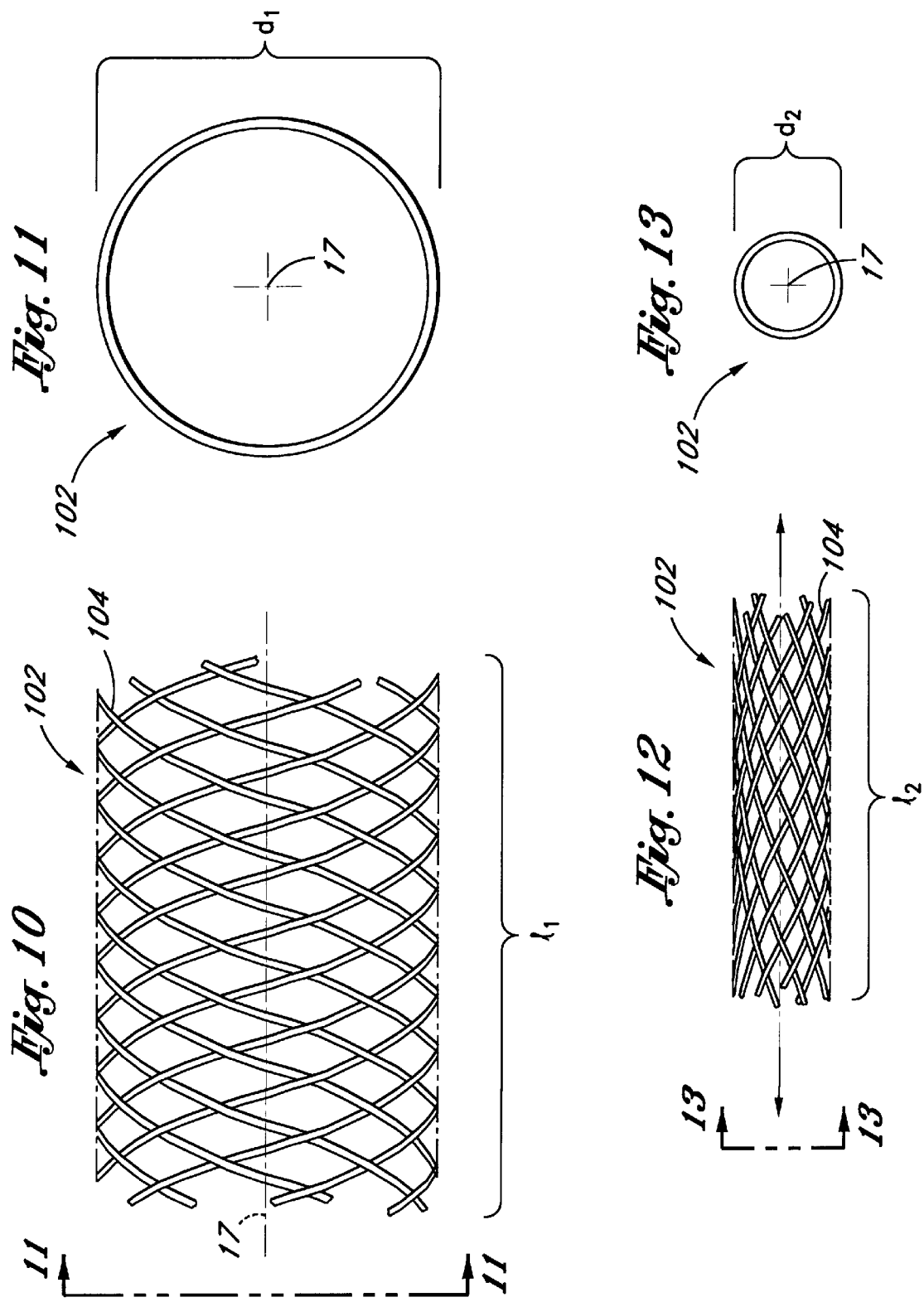

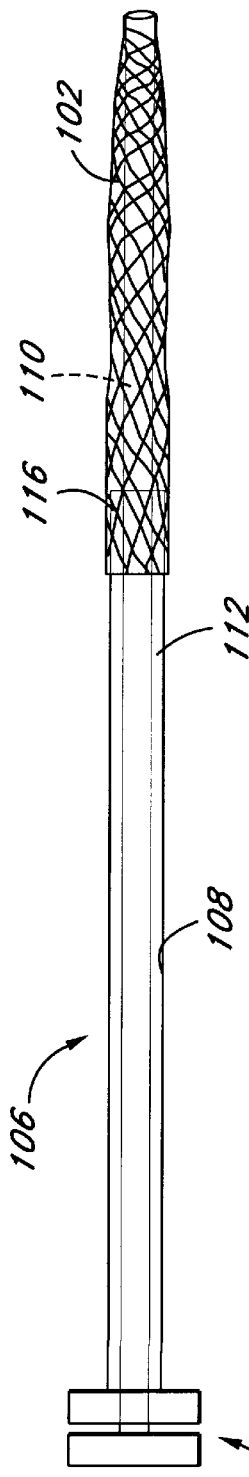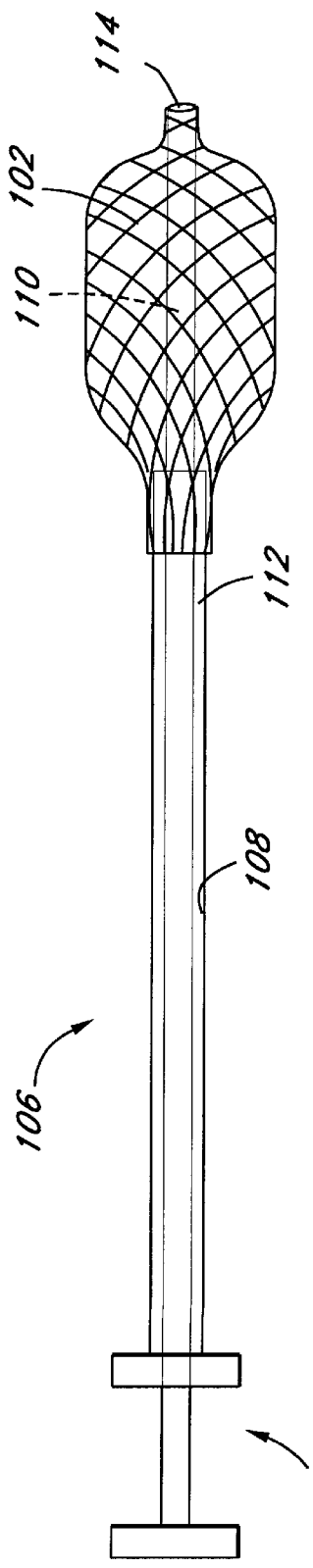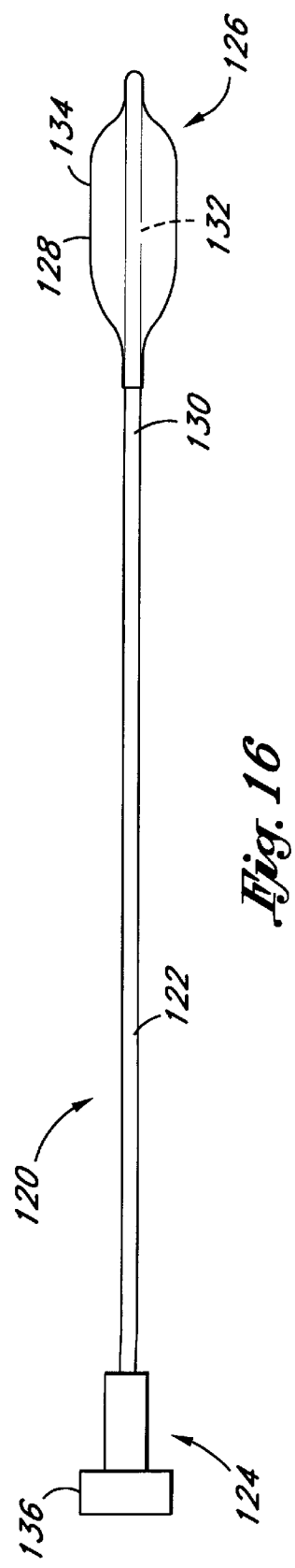

DUAL CATHETER RADIATION DELIVERY SYSTEM

The present application is a continuation-in-part of pending application Ser. No. 08/994,919 filed on Dec. 19, 1997, entitled Deployable Source Radiation Catheter.

BACKGROUND OF THE INVENTION

This invention relates to catheters useful to deliver radiation to prevent or slow restenosis of an artery traumatized such as by percutaneous transluminal angioplasty (PTA).

PTA treatment of the coronary arteries, percutaneous transluminal coronary angioplasty (PTCA), also known as balloon angioplasty, is the predominant treatment for coronary vessel stenosis. Approximately 300,000 procedures were performed in the United States in 1990 and nearly one million procedures worldwide in 1997. The U.S. market constitutes roughly half of the total market for this procedure. The increasing popularity of the PTCA procedure is attributable to its relatively high success rate, and its minimal invasiveness compared with coronary by-pass surgery. Patients treated by PTCA, however, suffer from a high incidence of restenosis, with about 35% or more of all patients requiring repeat PTCA procedures or by-pass surgery, with attendant high cost and added patient risk.

More recent attempts to prevent restenosis by use of drugs, mechanical devices, and other experimental procedures have had limited long term success. Stents, for example, dramatically reduce acute reclosure, and slow the clinical effects of smooth muscle cell proliferation by enlarging the minimum luminal diameter, but otherwise do nothing to slow the proliferative response to the angioplasty induced injury.

Restenosis is now believed to occur at least in part as a result of injury to the arterial wall during the lumen opening angioplasty procedure. In some patients, the injury initiates a repair response that is characterized by hyperplastic growth of the vascular smooth muscle cells in the region traumatized by the angioplasty. Intimal hyperplasia or smooth muscle cell proliferation narrows the lumen that was opened by the angioplasty, regardless of the presence of a stent, thereby necessitating a repeat PTCA or other procedure to alleviate the restenosis.

Preliminary studies indicate that intravascular radiotherapy (IRT) has promise in the prevention or long-term control of restenosis following angioplasty. IRT may also be used to prevent or delay stenosis following cardiovascular graft procedures or other trauma to the vessel wall. Proper control of the radiation dosage, however, appears to be important to inhibit or arrest hyperplasia without causing excessive damage to healthy tissue. Overdosing of a section of blood vessel can cause arterial necrosis, inflammation, hemorrhaging, and other risks discussed below. Underdosing will result in inadequate inhibition of smooth muscle cell hyperplasia, or even exacerbation of hyperplasia and resulting restenosis.

The prior art contains many examples of catheter based radiation delivery systems. The earliest systems disclose seed type sources inside closed end tubes. An example of this type of system can be found in U.S. Pat. No. 5,199,939 to Dake. In order to separate the radiation source from the catheter, a delivery system is disclosed by U.S. Pat. No. 5,683,345 to Waksman et al. where radioactive source seeds are hydraulically driven into a blind end catheter where they remain for the duration of the treatment, after which they are pumped back into the container. Later disclosures integrated the source wire into catheters more like the type common in interventional cardiology. In this type of device, a closed end lumen, through which is deployed a radioactive source wire, is added to a conventional catheter construction. It is supposed that the radioactive source wire would be delivered through the catheter with a commercial type after loader system produced by a manufacturer such as Nucletron, BV. These types of systems are disclosed in Liprie U.S. Pat. No. 5,618,266, Weinberger U.S. Pat. No. 5,503,613, and Bradshaw U.S. Pat. No. 5,662,580.

The systems disclosed in the prior art are all similar in that the source resides in the center of the lumen during treatment. The result of this is that the source energies must be higher in order to traverse the lumen of the blood vessel to get to the target tissue site in the vessel wall. Higher energy sources can have undesirable features; first, likelihood of radiation inadvertently affecting untargeted tissue is higher; second, the higher energy sources are more hazardous to the medical staff and thus require additional shielding during storage and additional precaution during use; third, the source may or may not be exactly in the center of the lumen, so the dose calculations are subject to larger error factors. This last factor was discussed at the 1997 American Heart Association Meeting session on Radiation Therapy. In a paper discussing a seed system similar to the ones disclosed above, Tierstein reported that a 3X differential dose factor can exist between the near vessel wall and the far vessel wall in an eccentrically placed source.

U.S. Pat. No. 5,059,166 to Fischell discloses an IRT method that relies on a radioactive stent that is permanently implanted in the blood vessel after completion of the lumen opening procedure. Close control of the radiation dose delivered to the patient by means of a permanently implanted stent is difficult to maintain because the dose is entirely determined by the activity of the stent at the particular time it is implanted. In addition, current stents are generally not removable without invasive procedures. The dose delivered to the blood vessel is also non-uniform because the tissue that is in contact with the individual strands of the stent receive a higher dosage than the tissue between the individual strands. This non-uniform dose distribution may be especially disadvantageous if the stent incorporates a low penetration source such as a beta emitter.

U.S. Pat. No. 5,302,168 to Hess teaches the use of a radioactive source contained in a flexible carrier with remotely manipulated windows. H. Böttcher, et al. of the Johann Wolfgang Goerthe University Medical Center, Frankfurt, Germany report in November 1992 of having treated human superficial femoral arteries with a similar endoluminal radiation source. These radioactive wire type methods generally require use of a relatively high activity source to deliver an effective dose. Accordingly, measures must be taken to ensure that the source is maintained reasonably near the center of the lumen to prevent localized overexposure of tissue to the radiation source. Use of these higher activity sources also dictates use of expensive shielding and other equipment for safe handling of the source.

Similar inventions have been disclosed that attempt to overcome the limitation of the seed based systems. Fearnot discloses a wire basket construction in U.S. Pat. No. 5,484,384 that can be introduced in a low profile state and then deployed once in place. Hess discloses a balloon with radioactive sources attached on the surface in U.S. Pat. No. 5,302,168.

Despite the foregoing, among many other advances in IRT, there remains a need for an IRT method and apparatus that delivers an easily controllable uniform dosage of radiation to the walls of the blood vessel without the need for special devices or methods to center a radiation source in the lumen.

SUMMARY OF THE INVENTION

The radiation delivery system of the present invention includes two catheters, an outer sheath balloon catheter and an inner radiation source catheter. In one embodiment, the inner radiation source catheter is also a balloon catheter. The outer sheath balloon catheter comprises single lumen tube with a balloon attached to the distal end. In one embodiment, the sheath balloon catheter is provided with a short guide wire lumen at its distal tip for rapid exchange placement. The proximal end of the sheath catheter is fitted with a touhy-borst style y-connector for outer balloon inflation and lumen access. Placement can be facilitated with a removable stiffening wire or stylet.

Once the sheath catheter is in place at a treatment site, a radiation balloon catheter is introduced through the y-connector into the lumen of the sheath catheter. The radiation balloon catheter is advanced to the treatment site through the lumen of the sheath catheter. This can be done under fluoroscopic guidance, using radiopaque markers commonly used for this purpose. The source balloon is then inflated, preferably with a dry medium such as $CO_2$, thus deploying the source up against the wall of the outer inflated balloon. When the treatment is completed, the source balloon is deflated and withdrawn. It may not even need to be sterilized, since there is no contact between the source catheter and the patient.

The source balloon preferably comprises thin film source mounted over the balloon with a cover layer. Alternatively, the balloon can be coated directly with an isotope with an optional cover layer over the isotope. However, a cover layer (such as a plastic) may not be necessary for this balloon, since the sheath catheter protects the patient from loose isotope particulate hazard.

In one embodiment, the source balloon is ion implanted or sputtered with silver ion. The silver is converted to AgCl in a solution of HCl and $NaClO_2$. The balloon is then dipped into a solution of Na125I, and the I-125 exchanges with the Cl and deposits on the balloon surface. This procedure produces a gamma emitting source in the 30 keV range, with a half life of about 60 days.

Alternatively, the source balloon can be ion implanted with Al and oxidized in $H_2O_2$ to form $Al_2O_3$ on the surface of the balloon. This is then dipped in a solution of $NaWO_4$. The WO4 ion binds to the $Al_2O_3$. This procedure produces a beta emitting source as the W-188 decays to Re-188, with energies in the 2.1 MeV range and a half like of about 70 days.

Alternatively, the balloon surface could be ion implanted directly with any radioactive isotope with an energy profile appropriate for treatment.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 1 is a partial, side elevational, cross-sectional view of a source wire in accordance with the present invention, positioned within a capture tube.

FIG. 2 is a side elevational view as in FIG. 1, with the capture tube proximally withdrawn to release a delivery zone on the source wire about the source center line.

FIG. 3 is a fragmentary view of a portion of the source wire illustrated in FIG. 2.

FIG. 4 is a side elevational, schematic view of a delivery catheter for containing the source wire and capture tube.

FIG. 5 is a side elevational view of a distal end of the delivery catheter positioned within a vessel, with the source wire positioned within the capture tube.

FIG. 6 is an enlargement of a distal portion of the catheter illustrated in FIG. 5.

FIG. 7 is a side elevational view as in FIG. 5, with the capture tube proximally retracted to deploy the radiation delivery zone within the balloon.

FIG. 8 is a side elevational, schematic view of an alternate delivery catheter, with the delivery wire in the axially elongated configuration.

FIG. 8a is a rapid exchange embodiment of the delivery catheter illustrated in FIG. 8.

FIG. 9 is an illustration of the catheter of FIG. 8, with the delivery wire in the radially enlarged configuration.

FIG. 10 is a side elevational schematic view of a braided tube for use with a radiation delivery catheter in accordance with a further aspect of the present invention, illustrated in an enlarged radial configuration.

FIG. 11 is an end view taken along the lines of 11—11 of FIG. 10.

FIG. 12 is a schematic illustration of the braided tube of FIG. 10, shown in an axially elongated and radially reduced configuration.

FIG. 13 is an end elevational view taken along the lines 13—13 of FIG. 12.

FIG. 14 is a side elevational view of a radiation delivery catheter utilizing the braided tube of FIGS. 10 through 13.

FIG. 15 is a side elevational view of the catheter of FIG. 14, with the braided tube in the axially reduced and radially enlarged orientation.

FIG. 16 is a side elevational view of an inner radiation source catheter, of the type useful for positioning within an outer sheath balloon catheter such as that illustrated in FIG. 4.

DETAILED DESCRIPTION OF THE PREFERRED EMBODIMENT

Referring to FIG. 1, there is schematically illustrated a radiation source wire 10 in accordance with the present invention. The source wire 10 comprises a proximal end 12 and a distal end 14. Adjacent the distal end 14 is a delivery zone 16, for delivering a radioactive dose.

The source wire 10 may comprise any of a variety of materials, suitable for delivering a radioactive charge. For example, the source wire may itself be a radioisotope such as yttrium. Alternatively, the source wire may be implanted with a radioisotope, using commercially available ion implantation equipment, or otherwise coupled to a radioisotope. Coupling can be accomplished in any of a variety of manners, such as by providing a cladding or coating over the source wire 10 in the area of the delivery zone 16, threading beads of a suitable material onto the source wire 10 in the delivery zone 16, winding the source wire 10 with a suitable material, and the like. In general, the source wire 10 is constructed from such materials or in such a manner that a delivery zone 16 can be activated for delivering a dose of radiation to a site in a body.

The radiation source may be composed of any alpha, beta or gamma particle emitting isotope. Preferably, however, the radioactive source is a pure beta-particle emitter for uniformity of dosing and minimum radiation hazard. Examples of such beta substances include Strontium-90, Rhenium-188 and Phosphorus-32. A gamma radiation source may be equally applicable, however, and examples of such are Gadolinium-153, Palladium-103, Iridium-192, and/or Iodine-125.

Any of a wide variety of isotopes can perform the restenosis inhibiting function of the present invention, as will be apparent to those of ordinary skill in the art in view of the disclosure herein. In general, relatively low energy gamma emitters or relatively high average energy beta emitters may exhibit sufficient activity and sufficient penetration to effectively inhibit smooth muscle cell proliferation. Although optimal energy can be determined through routine experimentation, it presently appears to the present inventors that a beta source with an average particle energy of about 700–900 keV $E_{avg}$ (approximately 1.7–2.3 MeV $E_{max}$) may achieve sufficient penetration at sufficient activity. Since gamma radiation has a deeper penetration per unit energy, only in the area of from about 5–50 keV particle energy may be sufficient to achieve a suitable penetration. Suitable penetration appears to be on the order of about 2 mm to about 8 mm or 10 mm, to adequately take into account the effects of asymmetric lesions, and highly calcified plaques. The activity of a selected isotope should be high enough to deliver an efficacious dose in the desired length of treatment time, taking into account the mass of isotope that can be deployed in a particular catheter design.

The amount and strength of the radioactive material contained in the combined number of loops of wire in the delivery zone 16 should be sufficient to deliver a desired dosage at a reference distance of 2 mm from the center of the source of from 100 to about 10,000 rads, (1 Gy to 100 Gy) preferably from about 1,000 rads (10 Gy) to about 2,500 rads (25 Gy), in about 2–10 minutes. The center of the source is identified by reference line 17 in FIGS. 2, 11 and 13. Radioactivity is generally measured in units of "Curie" (Ci), and the radioactivity of the material for the present invention is selected to provide he above dosage. For the preferred dosage, the radioactive material may have a radioactivity of approximately 10–500 mCi (milli curie) per centimeter of vessel to be treated, depending on the radiation source used.

Preferably, at least the delivery zone 16 of the source wire 10 comprises a shape memory metal, such as a nickel titanium alloy. Any of a variety of Nitinol alloys can readily be adapted for use in the present invention. The use of the shape memory metal permits the setting of a memory into the delivery zone 16 of the source wire 10, such that it is biased in the direction of a helical coil having a plurality of loops 26 as schematically illustrated in FIG. 2. Nitinol can be used for the entire length of the wire 10, or just for the delivery zone 16 in which case it is affixed to the distal end of a stainless steel wire or tube or other proximal segment.

Although the plurality of adjacent loops 26 in delivery zone 16 are illustrated in FIG. 2 as axially spaced apart, the optimal spacing, if any, between adjacent loops 26 is determined in view of the activity of the radio active carrier and the desired delivery time and dose for a particular application. For example, as the space between adjacent loops 26 in a delivery zone 16 is reduced, more surface area of the source wire 10 is available per unit length of the treatment site in the body lumen. Thus, a more tightly packed coil in delivery zone 16 will deliver a given dose of radiation in less time, or a higher dose in the same time, than a delivery zone 16 having a plurality of loops 26 with relatively larger axial separations therebetween. Reduced spacing in-between the adjacent loops will also produce a more uniform radiation penetration profile into the vascular wall. Thus, in one embodiment, the adjacent loops 26 are preferably substantially in contact with each other to produce a delivery zone 16 in the enlarged configuration with essentially a solid tubular wall. Alternatively, the space between adjacent loops 26 is no more than about two times the axial width of the source wire 10 in the area of the delivery zone 16, and, preferably, no more than about one axial width of the source wire 10.

One effect of the axial separation between adjacent loops 26 in the deployed configuration will be readily appreciated in light of the following example. In one embodiment of the invention, a wire 10 having a width in the axial catheter direction of 0.5 mm is utilized to form a tight-packed coil for treating a 2 cm lesion. The 0.5 mm wire will require 40 loops to extend over a 2 cm delivery zone. If the delivery zone is configured to expand to a 3 mm expanded diameter, the total expanded or linear length of the delivery zone 16 to accomplish a 2 cm delivery zone in the expanded profile is approximately 40×3×π or 37.7 cm of wire. Spacing the adjacent loops 26 only a single diameter apart reduces the linear length of the wire necessary to produce the 2 cm length 3 mm diameter expanded delivery zone 16 by one-half. Optimizing this aspect of the invention should be accomplished taking into account the activity of the radiation source, the length of the lesion to be treated, the diameter of the delivery zone 16 in the deployed configuration, as well as delivery device issues such as the coefficient of static friction between the source wire 10 and the central lumen 24 of the sleeve 18.

The source wire 10 may have any of a variety of cross-sectional configurations as will be apparent to those of skill in the art in view of the disclosure herein. For example, source wire 10 may have a circular cross section with a diameter in the range of from about 0.005 inches to about 0.05 inches or greater, depending upon the intended clinical use. Alternatively, at least the delivery zone 16 and possibly the entire length of the source wire 10 comprises a generally rectangular cross-sectional configuration as schematically illustrated in FIGS. 2 and 3. The illustrated source wire 10 has in at least the delivery zone 16 a short cross-sectional thickness dimension 13 in the radial direction within the range of from about 0.002 to about 0.010, and a long cross-sectional width dimension 11 in the axial direction within the range of from about 0.005 to about 0.100 or greater. The rectangular configuration may be preferable to round since it can increase the surface area of the delivery zone which is directly adjacent the vessel wall or interior wall of the delivery balloon as will be discussed.

The surface area of the wire appears more important than the cross-sectional area for the purpose of radiation delivery, and any of a variety of surface area wires can be utilized depending upon the desired radioactive dose, delivery time, device flexibility, and other considerations which will be apparent to those of skill in the art in view of the disclosure herein. For example, a round wire 10 in the delivery zone 16 having a diameter of about 0.010 inches has a surface area of about 0.0314 square inches per running inch of wire. Using the same units, a round wire having a diameter 0.020 inches produces a surface area of 0.0628 square inches and a round wire having a diameter of 0.015 inches has a surface area of about 0.047 inches. Flat wires or ribbons can also be utilized, and, for example, a flat wire having a cross-section of about 0.010 by 0.005 inches has a surface area of about 0.030 square inches per running inch of flat wire. Using the same units, a flat wire having dimensions of about 0.015 inches by about 0.005 inches has a surface area of about 0.040 square inches, and a flat wire having dimensions of about 0.020 inches by about 0.005 inches has a surface area of about 0.050 square inches. The precise surface area for any particular application can be optimized through routine experimentation by those of skill in the art in view of the disclosure herein.

Preferably, the preset source wire 10 in the delivery zone 16 is biased in the direction of a cylindrical coil having a diameter within the range of from about 2 mm to about 5 mm or greater, depending upon the diameter of the target vessel. In general, the relaxed (enlarged) diameter of the coil is preferably slightly larger than the diameter of the intended vessel, so that the plurality of loops 26 will seat against the vessel wall or inside of the delivery balloon which will be discussed. A single diameter coil in delivery zone 16 can be utilized to treat a variety of diameters of vessels, as will be apparent to those of skill in the art, with the source wire 10 merely springing to a smaller diameter expanded configuration when used in relatively smaller arteries.

Preferably, the source wire 10 is axially movably disposed within an outer tubular capture tube or sleeve 18. Sleeve 18 is provided with a proximal end 20, a distal end 22 and a central lumen 24 extending therethrough. The sleeve 18 may be utilized to retain the delivery zone 16 of the source wire 10 in a generally linear or stretched configuration as schematically illustrated in FIG. 1. Proximal axial retraction of the sleeve 18 with respect to the source wire 10 causes the delivery zone 16 to exit the distal end 22 of the sleeve 18, and resume its preset enlarged coiled configuration as illustrated in FIG. 2.

Sleeve 18 can have any of a variety of inside diameters, depending upon the dimensions of the source wire 10, and the degree of elasticity and other memory characteristics of the delivery zone 16. For example, if the material of the source wire 10 permits the source wire 10 to be stretched into a generally axial configuration in the delivery zone 10, the inside diameter of central lumen 24 can approach the outside dimensions of the source wire 10 with a few thousandths of an inch tolerance for slidability. If, however, the memory characteristics of the source wire 10 require that the delivery zone 16 be straightened no more than a certain sinusoidal pattern such as is illustrated in FIG. 1, the inside diameter of central lumen 24 should be dimensioned accordingly. Optimization of the inside diameter of central lumen 24 in cooperation with a particular source wire 10 can be readily accomplished through routine experimentation by those of skill in the art in view of the disclosure herein.

The outside diameter of sleeve 18 is preferably minimized, to permit the sleeve 18 to be advanced transluminally to remote and possibly torturous treatment sites. Preferably, the sleeve 18 has an outside diameter within the range of from about 2 F. (0.026") to about 4 F. (0.052") and, for typical coronary artery applications in vessels having an inside diameter of approximately 3 mm, the sleeve 18 preferably has a diameter of no more than about 5 F. (0.067").

The length of the sleeve 18 depends upon the desired application. For example, lengths in the area of from about 120 cm to about 140 cm are typical for use in percutaneous transluminal coronary angioplasty applications, using a femoral artery access site.

The tubular sleeve 18 may be produced in accordance with any of a variety of known techniques for manufacturing vascular access catheter bodies, such as by extrusion of appropriate biocompatible plastic materials. Any of a variety of materials, such as polyethylene, PEBAX, nylon, polyethylene terephthalate, polyimide and others may be used for this purpose. Alternatively, at least a portion or all of the length of the sleeve 18 may comprise a spring coil, solid walled hypodermic needle tubing, or braided reinforced wall as will be understood in the catheter and guidewire arts. The sleeve 18, either alone or in combination with a delivery catheter 30, must have sufficient structural integrity (e.g., "pushability") to permit the sleeve 18 to be advanced to distal arterial locations without buckling or undesirable bending of the sleeve 18.

Lubricous coatings or low-friction surfaces may be particularly desirable on the interior wall of the central lumen 24 in the region of the delivery zone 16, to facilitate axial displacement of the delivery zone 16 with respect to the sleeve 18. Suitable lubricous coatings include polytetrafluoroethylene, Paralene and hydrogels.

Referring to FIG. 4, there is disclosed a delivery catheter 30, which may be used to facilitate placement of the delivery zone 16 at a vascular treatment site. The delivery catheter 30 generally comprises a proximal end 32 and a distal end 34. An elongate flexible tubular body 36 extends at least intermittently therebetween. A central lumen 38 extends axially from the proximal end 32 at least as far as a distal opening 46, which provides communication between the central lumen 38 and an inflatable balloon 48.

The proximal end 32 of the delivery catheter 30 is provided with a manifold 40 as is well-known in the art. Manifold 40 comprises at least a primary access port 42 for providing communication with the central lumen 38. Preferably, a secondary access port 44 is also provided. Secondary access port 44 is in the illustrated embodiment in fluid communication with the central lumen 38, and may be utilized to inject inflation media into the balloon 48 by way of lumen 38. Thus, the illustrated delivery catheter is a single lumen catheter, although dual-lumen, triple-lumen, or other multi-lumen designs may be readily utilized depending upon the desired capabilities of the catheter.

The distal end 34 of the delivery catheter 30 is provided with an inflatable balloon 48. The balloon 48 is secured at a proximal neck 50 to a distal end of a proximal segment of the tubular body 36. A distal neck 52 is secured to a proximal end of a distal segment 54. Distal segment 54 in the illustrated embodiment is provided with a proximal guidewire access port 60, which communicates by way of a guidewire lumen 56 with a distal guidewire access port 58. In this manner, the delivery catheter 30 can be tracked along a conventional guidewire 62, without the need for the guidewire to traverse the interior of balloon 48 for reasons which will be understood based upon the disclosure herein.

In general, the tubular body 36 in accordance with the present invention is provided with a generally circular cross-sectional configuration having an external diameter within the range of from about 0.03 inches to about 0.065 inches. In diameter of about 0.042 inches (3.2 F.) throughout most of its length. Alternatively, noncircular cross-sectional configurations may also be utilized, depending upon the method of manufacture and the intended use.

In a catheter intended for peripheral vascular applications, the tubular body 36 would typically have an outside diameter within the range of from about 0.039 inches to about 0.065 inches. In coronary vascular applications, the tubular body 36 will typically having an outside diameter within the range of from about 0.030 inches to about 0.045 inches.

Diameters outside of the preferred ranges may also be used, provided that the functional consequences of the diameter are acceptable for the intended purpose of the catheter. The tubular body 36 can be manufactured in accordance with any of a variety of known techniques using known materials for the construction of balloon-tipped catheter bodies. For example, extrusion of any of a variety of known biologically-compatible materials can readily be accomplished. Suitable materials include, among others, high density and low density polyethylenes, and others disclosed previously in connection with the tubular sleeve 18.

The balloon 48 may comprise any of a variety of balloon materials well known in the angioplasty catheter art. For example, generally noncompliant materials such as polyethylene terephthalate may be used. Alternatively, relatively compliant materials such as medium density polyethylene, linear low-density polyethylene, nylon, polyester, or any of a variety of medical-grade polymers known for this use in the art may be used. Although not preferred, a fully compliant balloon could be used as well, such as one made from latex or silicon (or other elastomer). In general, the balloon 48 may be constructed to withstand high pressures on the order of at least about 10 to 14 atmospheres without any leakage or rupture. Such balloons can be utilized to accomplish a dilatation of a stenotic lesion in an artery prior to, during or following the radiation delivery. Alternatively, the balloon 48 may be constructed to withstand only relatively low pressures, in which event the balloon 48 would be utilized merely to inflate to the diameter of the surrounding vessel wall but without seeking to accomplish any luminal dilatation.

The central lumen 38 in the delivery catheter 30 is dimensioned to axially slidably receive the tubular sleeve 18. Thus, the distal end 22 of sleeve 18 can be introduced into the primary access port 42 and advanced throughout the length of the delivery catheter 30 as is illustrated in partial view in FIG. 5.

In use, the source wire 10 is percutaneously introduced into the vascular system and transluminally advanced to a treatment site. During the introduction and advancing steps, the delivery zone 16 of the source wire 10 is restrained in a reduced cross-sectional profile as illustrated in FIGS. 1, 5 or 6. Once the delivery zone 16 is positioned about the treatment site, the sleeve 18 is retracted proximally with respect to the source wire 10, to permit the source wire 10 in the delivery zone 16 thereof to expand to its enlarged cross-sectional profile.

The sleeve 18 and source wire 10 may be transluminally advanced as a unit through the vasculature and positioned at a treatment site either by itself, or, preferably, through the use of a delivery catheter such as the illustrated delivery catheter 30. The use of a delivery catheter 30 is preferred, so that the delivery zone 16 of the source wire 10 is at all times entrapped within a balloon 48, thereby minimizing the risk of a portion of the source wire 10 or radioactive elements attached to the source wire 10 breaking off and remaining in the vessel.

Referring to FIG. 5, there is illustrated the delivery catheter 30 positioned within a vessel wall 64. The source wire 10 is illustrated in its reduced cross-sectional profile within the sleeve 18. The distal end 22 of sleeve 18 is positioned within a recess 68 at the distal end of the balloon 48. Recess 68 terminates at its distal end in a plug or occlusion 70, which may be formed, for example, through the use of any of a variety of suitable thermoplastic materials.

To enhance the pushability of the delivery catheter 30, the sleeve 18 may be positioned within the central lumen 38 prior to introduction into the patient. Axial distal force is transmitted from the sleeve 18 to the distal segment 54 in the area of recess 68 as will be apparent to those of skill in the art. Once the balloon 48 has been positioned adjacent the treatment site, the sleeve 18 may be proximally withdrawn from the recess 68 while the wire 10 is axially retained to enable the source wire 10 to radially expand within the balloon as is illustrated in FIG. 7. Alternatively, alternate column strength structures may be provided in the region of the balloon 48, and the sleeve 18 and source wire 10 can be introduced into the delivery catheter 30 following placement of the balloon 48 at the treatment site.

Referring to FIGS. 8 and 9, another embodiment of the present invention is disclosed. An elongate flexible catheter 70 has a proximal end 72 and a distal end 74. The catheter 70 comprises an outer tubular body 76 having a proximal end 78 and a distal end 79. An elongate lumen 80 extends throughout the length of the outer tubular body 76. Suitable dimensions, materials and manufacturing techniques for the catheter 70 have been discussed above.

An inner tubular body 82 is disposed within the central lumen 80, in at least a distal portion of the catheter 70. In the illustrated embodiment, the inner tubular body 82 extends from a proximal end 84 at the proximal end 72 of the catheter 70, throughout the length of the catheter 70 to a distal end 86. In an alternate embodiment (not illustrated) the coaxial relationship between the inner tubular body 82 and outer tubular body 76 extends only distally of a transition in the catheter 70. Proximal to the transition, the catheter 70 may comprise a multi-lumen extrusion, having side-by-side guidewire and inflation lumens or others as will be apparent to those of skill in the art. The transition may occur within about 10 cm or 20 cm of the distal end 86 of the tubular body 82.

In the illustrated embodiment, a balloon 88 is provided near the distal end 74 of the catheter. The balloon 88 is secured at its proximal end to the distal end 79 of the outer tubular body 76. A distal end of the balloon is secured to the distal end 86 of the inner tubular body 82. In this manner, the annular lumen 80 formed between the inner tubular body 82 and the outer tubular body 76 is in fluid communication with the interior of the balloon 88.

The proximal end 72 of the catheter 70 is provided with a manifold 90 made in accordance with techniques well known in the art. Manifold 90 may have any of a variety of access ports or controls, depending upon the desired functionality of the catheter 70. In the illustrated embodiment, manifold 90 is provided with a guidewire access port 92 which provides access to an elongate guidewire lumen 94 extending throughout the length of the inner tubular body 82 as will be understood in the art. An inflation port 94 provides fluid communication with the interior of balloon 88 by way of the lumen 80. In addition, a deployment port 96 provides access for a deployment element 98 such as a wire or other control to permit reciprocal axial motion of the radiation delivery wire 100 as will be discussed.

The over the wire embodiment illustrated in FIGS. 8 and 9 can readily be configured as a rapid exchange embodiment such as that illustrated in FIG. 8a. In the rapid exchange embodiment, the guidewire lumen 94 extends between a distal guidewire access port 95 and a proximal guidewire access port 93. The proximal guidewire access port 93 is positioned along the length of the tubular body 76, at a point spaced distally apart from the manifold 90. Generally, the proximal access port 93 will be positioned within about 10 cm or 20 cm of the distal end of the catheter. The minimum distance between the proximal port 93 and the balloon can be calculated based upon the number of revolutions of radiation wire 100 in the enlarged configuration, and the axial length necessary to accommodate the radiation wire 100 when in the reduced profile configuration as illustrated in FIGS. 8 and 8*a*. Rapid exchange embodiments such as that illustrated in FIG. 8*a* can be readily constructed using techniques well known to those of skill in the art in view of the disclosure herein.

A radiation delivery wire 100 is moveable between an axially elongated, low profile orientation as illustrated in FIG. 8 and a radially expanded, axially shortened configuration as illustrated in FIG. 9, by reciprocal axial movement of the deployment element 98. In FIG. 8, the radiation wire 100 is illustrated as wrapped helically around the inner tubular body 82 to minimize the introduction profile of the device. The radiation delivery wire 100 extends proximally of the distal end 79 of the outer tubular body for a sufficient distance to accommodate the axial length of wire necessary to produce the desired enlarged profile as illustrated in FIG. 9. Although the illustration in FIG. 9 shows only two or three full revolutions of the radiation delivery wire 100 within the balloon 88, it will be understood that the enlarged configuration of the radiation delivery wire 100 will be more likely in the form of a tightly packed coil, having a large number of revolutions within the balloon with little or no axial separation between adjacent loops, to optimize the radiation delivery characteristics as has been discussed.

In an embodiment having a nitinol or other shape memory metal based radiation delivery wire 100, the coil is in the Martensite form in the reduced profile configuration of FIG. 8. In one embodiment, the nitinol wire has a transition temperature in the area of about 30° C. Positive proximal traction may be applied to the deployment element 98 during the introduction of the catheter into the body, if desired, to ensure that the radiation delivery wire 100 retains its lowest possible crossing profile. Once the balloon 88 has been positioned at the treatment site, the balloon is inflated with inflation media warmed to a temperature such as about 40° C. which is not harmful to the body and which will transition the nitinol to move to its preset coiled configuration (illustrated in FIG. 9) due to the force generated as the wire transitions from the Martensite structure to an Austenite structure. This transition will cause the deployment element 98 to advance axially in a distal direction to accommodate the larger circumference of the windings of the radiation delivery wire 100 within the balloon. The axial distal displacement of deployment element 98 may occur solely under the force generated by the nitinol transition, or may be facilitated by the clinician applying distal force to the deployment element 98 or other control.

To remove the catheter 10 from the treatment site, the deployment element 98 may be proximally retracted to collapse the delivery wire 100 back into a tight wrapped configuration around the inner tubular body 82, and the balloon may be reduced by aspiration of the inflation media. Return to the low profile orientation of the balloon 88 may be facilitated by a subsequent step if introducing a low temperature fluid into the balloon (e.g., on the order of no higher than about 20–25° C.) thereby causing the wire to transition back to its Martensite form, which is a more malleable condition and will facilitate the axial elongation and radially reduction of the helical radiation delivery wire 100. The device may then be removed from the treatment site.

Any of a wide variety of modifications to the specific foregoing structure and methodology may be readily accomplished as will be understood to those of skill in the art in view of the disclosure herein. For example, the manifold 90 may be provided with any of a variety of controls, such as rotatable knobs, levers, slider switches, electronically activated drive systems, and the like, which can produce an axial proximal and distal motion on the deployment element 98. The deployment element 98 may comprise any of a variety of structures, such as a wire or ribbon as illustrated. Alternatively, the deployment element 98 may comprise a tubular body, concentrically disposed about the inner tubular body 82 and within the outer tubular body 76. A distal end of the deployment element in the case of a tubular deployment element 98, will be affixed to the proximal end of the radiation delivery wire 100. The transition 99 between the proximal end of the radiation delivery wire 100 and the distal end of the deployment element 88 should be axially positioned to take into account the length of the wire 100 when in the reduced configuration as illustrated in FIG. 8.

In addition, the outer balloon 88 can be omitted from the design, if desired, so that the radiation delivery wire 100 in its expanded configuration is coiled directly adjacent to the vessel wall.

The embodiment illustrated in FIGS. 8 and 9, similar to previous embodiments, can be utilized in a variety of different methods. For example, the balloon 88 can be utilized simply to entrap the radiation delivery wire 100. Alternatively, the balloon 88 can be utilized to accomplish percutaneous transluminal angioplasty at generally higher pressures, such as anywhere within a range of from about 8 atmospheres to about 20 atmospheres. The method of utilizing the catheter 70 to accomplish both PTA and irradiation can be performed by transluminally positioning and inflating the balloon 88 at a stenotic site to perform PTA for a suitable inflation period and subsequently enlarging the radiation delivery wire 100 against the interior wall of the balloon 88, or the PTA dilatation and irradiation can be accomplished simultaneously.

Any of a variety of other functionalities can be readily added to the catheter 70 depending upon the desired clinical methodology, as will be readily apparent to those of skill in the art in view of the disclosure herein. For example, a central axially extending perfusion conduit may be provided through the center of the balloon 88, having at least one proximal perfusion port on the catheter body 70 in fluid communication across the balloon with at least one distal perfusion port near the distal end 86 of the inner tubular body 82. In this manner, blood is allowed to perfuse across the balloon 88 while the balloon is inflated.

Alternatively, or in addition, drug delivery capability may be added to the catheter 70 using any of a variety of drug delivery designs. In one embodiment, a double balloon may be utilized, in which the outer balloon is perforated and the space between the outer and inner balloons is in fluid communication with the manifold 90 by way of a drug delivery lumen (not illustrated). In this manner, medication can be introduced into the space between the inner and outer balloons, and through the drug delivery ports on the outer balloon to the vessel wall. Drug delivery can be accomplished during, before or after radiation delivery and/or PTA. Suitable drug delivery structures include those disclosed in U.S. Pat. No. 5,295,962 to Crocker et al., the disclosure of which is incorporated in its entirety herein by reference. The foregoing multifunctional capabilities and structures of the embodiment of FIGS. 8 and 9, such as drug delivery and dilatation (PTA), can also be readily incorporated into the embodiments illustrated in FIGS. 1 through 7 as will be apparent to those of skill in the art in view of the disclosure herein.

Referring to FIGS. 10–14, an alternate embodiment of a radiation delivery wire configuration is disclosed. A braided tube 102 is constructed of multiple helical elements 104 such as round wire or flat ribbon as has been discussed in connection with previous embodiments. Round wire having a diameter in the range of from about 0.001 inches to about 0.009 inches, for example may be used.

The orientation of the multiple elements 104 in the braided tube 102 enable the tube to have a first diameter d1 at a first axial length 11 as illustrated in FIGS. 10 and 11, which diameter is reducible to a second smaller diameter d2 at a second longer axial length 12 as illustrated in FIGS. 13 and 14. Thus, the braided tube 102 can be axially elongated to reduce its cross sectional area such as for percutaneous insertion and transluminal advancement to a treatment site, and the braided tube 102 can be radially enlarged and axially reduced in length to assume the configuration illustrated in FIGS. 10 and 11.

Axial elongation and reduction of the braided tube 102 can be accomplished either by conversion between the Martensite and Austenite forms in a shape memory metal such as Nitinol, or by applying an axial proximal traction on the proximal end of the tubular braid 102 with respect to the distal end to assume the reduced cross sectional profile and by applying distal axial pressure on the proximal end of the tubular braid 102 with respect to the distal end to assume the radially enlarged profile. A similar structure for a different purpose can be seen, for example, in U.S. Pat. No. 4,655,771 to Wallsten, the disclosure of which is incorporated in its entirety herein by reference.

The surface area available for active isotope coating on the braided tube 102 can be varied by varying the pitch angle of the elements 104, the diameter of the elements 104, and/or the number of elements 104 in the weave.

In calculating the available surface area, the following variables are utilized:

h=the helical length per turn of the element about the tube

φ=the tube diameter or root diameter r=the run length or axial pitch of an element L=the total balloon length θ=the pitch angle of the element Ψ=the element diameter P=the number of elements in the braid Because the lengths and angles involved in the calculations can be approximated using triangles, the following calculations can be solved wherever two sides and an angle are known. Thus, calculating the surface area available may be performed as follows.

First, the helical length per turn of the element 104 about the tube is calculated. The circumference of the tube is calculated as (2π*radius) or (π*φ) in terms of the above variables. As the element completes one revolution about the circumference of the tube, the helical length of the turn may be illustrated as the hypotenuse of a triangle in which the side opposite the angle θ is the circumference of the tube and the side adjacent the pitch angle is the axial pitch of the element. Thus, equation 1 illustrates the relationship between the pitch angle θ, the circumference of the tube and the helical length of one turn about the tube.

$$\sin\theta = \frac{\pi\phi}{h} \quad [1]$$

Thus, the length of the hypotenuse, h, which represents the helical length per turn of the element about the tube is solved for from equation 1 to yield equation 2.

$$h = \frac{\pi\phi}{\sin\theta} \quad [2]$$

The number of helical turns which occur in the length of the braid is calculated in a similar fashion. The length of the braid, L, and the hypotenuse form the angle θ between them. Accordingly, the opposite side of the triangle is the number of turns, N, multiplied by the circumferential distance around the tube.

$$\tan\theta = \frac{N\pi\phi}{L} \quad [3]$$

Thus, the number of turns, N, which occur in the length, L, of the braid may be solved form equation 3 which yields equation 4.

$$N = \frac{L\tan\theta}{\pi\phi} \quad [4]$$

Knowing the helical length per turn, h, and the total number of turns, N, for the length of the braid, the total length of the helical turns, H, for the length of the braid may now be solved for as in equation 5.

$$H = h * N = \left(\frac{\pi\phi}{\sin\theta}\right) * \left(\frac{L\tan\theta}{\pi\phi}\right) \quad [5]$$

Therefore, the total helical length, H, of each element is:

$$H = \frac{L}{\cos\theta} \quad [6]$$

where L is the length of the balloon and θ is the pitch angle of the element.

Next, the surface area, $A_f$, along the helical length, H, of each element is calculated. The surface area of a cylinder is simply the circumference of the cylinder multiplied by the length of the cylinder. Thus, where the length of the element is H and the diameter is Ψ, the surface area of a wire is (π Ψ H). The following calculations will also assume that the wire is on a tube of length L and a pitch angle of θ. Substituting the equality for H from equation 6 into the equation for surface area of a wire yields equation [7].

$$A_f = \frac{\pi\psi L}{\cos\theta} \quad [7]$$

Knowing the surface area along the helical length, H, of the element, the total surface area of an entire solid braid can be calculated once the total number of elements in the braid is known. The total surface area, $A_{TOT}$, of all of the elements without any overlap is $A_f \times P$, where P is the number of elements in the weave. So:

$$A_{TOT} = A_f \times P \quad [8]$$

Substituting the equality for $A_f$ of [7] into [8] yields [9]:

$$A_{TOT} = \frac{\pi \psi L P}{\cos \theta} \quad [9]$$

For example, consider a 3.0 mm diameter tube having a length of 20 mm and a pitch angle of 45°. The tube is surrounded by 20 round wire elements having diameters of 0.25 mm. The total surface area of the elements is 444 mm² as shown below.

$$A_{TOT} = \frac{\pi(.25 \text{ mm})(20 \text{ mm})(20)}{\cos 45°} = 444 \text{ mm}^2$$

The braided tube 102 described above can be provided with a radioactive charge in accordance with any of the techniques described previously herein. For example, the tube may comprise a material which is capable of emitting a radioactive charge. Alternatively, the tube can be ion implanted, doped, clad or otherwise provided with a radiation emitter. Cladding can be accomplished such as by dipping, spraying, sputter coating or any of a variety of other techniques which will be understood to those skill in the art.

Alternatively, radioactive carrier material can be mechanically affixed to the braid, such as by clamping, threading, or other techniques which can be used for beads or tubular elements. In any case, the activity of the source may be controlled by adjusting the variables $\Psi$, L, P, and/or $\theta$.

The braided tube 102 can be adapted to any of a variety of radiation delivery catheters, which are capable of permitting axial expansion and contraction of the tube 102. For example, referring to FIG. 14, there is illustrated a radiation delivery catheter 106. The catheter 106 generally comprises an elongate flexible tubular body 108 having a central lumen 112 extending axially therethrough. An inner tubular body 110 is axially movably positioned within the lumen 112. A distal end 114 of the inner tube 110 extends distally beyond the distal end 116 of the outer tube 108. A braided tube 102 is secured to the catheter 106 such that a proximal end of the braided tube 102 is secured to the distal end 116 of the outer tube 108. A distal end of the braided tube 102 is secured to a distal end 114 of the inner tube 110.

The proximal ends of the inner and outer tubes 110 and 108 terminate in a control 118. The control 118 is adapted to axially movably displaced the inner tube 110 with respect to the outer tube 108. Thus, for example, in FIG. 14, the braided tube 102 is illustrated in its reduced cross sectional configuration. Manipulation of the proximal control 118, as shown in FIG. 15, proximally retracts the inner tube 110 with respect to the outer tube 108, thereby shortening the axial length of the braided tube 102 and increasing its radial diameter. The configuration illustrated in FIG. 15 may then be utilized to directly administer a radioactive dose to the vessel wall.

The braided tube 102 may be utilized as illustrated, so that blood may perfuse through the spaces between the various adjacent elements 104 of the braided tube 102. Alternatively, the braided tube 102 may be provided within an outer balloon (not illustrated) which can be secured at its proximal end to the outer tube 108 and at its distal end to the inner tube 110 as will be apparent in view of the disclosure herein.

In accordance with a variation of the present invention, there is disclosed a source catheter 120 for carrying a radiation source 134. See FIG. 16. In general, the source catheter 120 is axially moveably positionable within an outer sheath catheter such as the catheter 30 illustrated in FIG. 4.

The source catheter 120 comprises an elongate flexible tubular body 122, having a proximal end 124 and a distal end 126. Distal end 126 is provided with a radially enlargeable structure such as a balloon 128. The balloon is in communication with a central lumen 130, by way of at least one aperture 132 in the catheter shaft. Thus, the balloon can be inflated by coupling a source of inflation media (not illustrated) to an inflation port on proximal manifold 136, which is in communication with lumen 130.

Although illustrated in the context of an inflatable balloon source catheter 120, any of a variety of alternate structures can be utilized to carry a radially expandable or enlargeable radiation source into the balloon on an outer sheath catheter, such as those structures disclosed elsewhere herein. In general, the function of the source catheter 120 is to carry a radioactive source 134 through the lumen in an outer sheath catheter such as catheter 30. The source catheter 120 is then able to radially expand in a distal portion thereof, to position a radiation source adjacent the interior wall of the balloon 48 on the sheath catheter 30. The radiation source is thereafter capable of radial reduction in size, and withdrawal from the outer sheath catheter 30. Alternatively, the inner source catheter 120 and outer sheath catheter 30 can be simultaneously withdrawn from a treatment site.

With respect to an embodiment of the inner source catheter 120 which includes an inflatable balloon 128 as the radially enlargeable structure, the radioactive source 134 may be secured to or within the balloon 128 in any of a variety of manners. For example, the balloon 128 can be provided with an outer thin film source, such as that disclosed in U.S. patent application Ser. No. 09/025,921, to Trauthen, et al. filed Feb. 19, 1998, entitled Thin Film Radiation Source, the disclosure of which is incorporated in its entirety herein by reference.

As disclosed therein, a thin film substrate (e.g. Mylar® (polyester), Kapton® (polyimide) or PET) may be treated with a tie layer composed of a three-dimensional matrix with an ionic compound. This is sometimes referred to as an ion exchange surface. The choice of the ionic compound is made to encourage the ion desired to bond within the tie layer.

In one embodiment, the three-dimensional matrix is polyvinyl pyrolidone (PVP) with an ionic compound containing a Br ion. The PVP matrix is commonly used in hydrophilic coatings and as a carrier for $I_2$ in antimicrobial applications. The three-dimensional matrix is designed to hold and increase the concentration of ionic compound on the surface. Direct attachment of the ionic compound would result in layers on the molecular scale. To accomplish attachment, the treated substrate is placed in an ionic solution of I-125 (Na $^{125}$I, a commercially available form of I-125). The I-125 ion exchanges with the Br ion from the PVP, thus incorporating itself into the tie layer. Thus a gamma radiation source is produced. This system can work alternatively in an ionic solution of P-32 ($H_3{}^{32}PO_4$ a commercially available form of P-32) to form a beta emitting source.

In one specific embodiment of the present invention, a generally rectangular polyester sheet having a width of about 2 cm, a length of about 3 cm and a thickness of about 12 microns was coated with a PVP ion exchange surface and soaked in a 0.125 wt % I-125 in NaI solution. The resulting source was thereafter wrapped around a balloon having an inflated diameter of about 3.0 mm and an axial length of about 30 mm. The sheet length of 3 cm allowed the source to be wrapped around the inflated balloon approximately 3 full revolutions. Thus, in this context, sheet length corresponds to the circumferential direction as wrapped around the balloon, and sheet width corresponds to the axial length of the source along the balloon. In this embodiment, the activity of the source was approximately 110 milliCuries per centimeter length of the substrate sheet. Thus, by providing three full revolutions, a net activity of about 330 milliCuries was produced. Using the present invention, the net activity could conveniently be doubled, for example, by lengthening the substrate sheet to about 6 cm, thereby enabling six revolutions of the substrate around the balloon. This may accomplish a respective reduction in treatment time of 50%.

In cases where adequate activity can be achieved with a single wrap of the source, a thin tube could be used alternatively to the sheet. For example, PET tubing can be commercially obtained with wall thicknesses similar to the sheet material described earlier (0.0003–0.001"). The tube construction may allow for simpler assembly, but otherwise possesses the same properties.

The nature of the tie layer 14 will depend on the isotope to be attached. Many different coatings and attachment technologies are available, and new ones can be readily adapted for use in the present invention. For example, Iodine-125 (I-125) can be bound to a substrate by passing it over the substrate coated with a polyvinyl pyrolidone (PVP) as discussed previously. In yet another system the isotope may be incorporated directly into a matrix coating and cured or adhered to the surface in one step. These attachment technologies are known and commercially available.

In another type of system that can be constructed, the tie layer 14 can incorporate a metal exchange surface, which will attach Pd-103 in the form of palladium metal drawn directly from solution. For example, the substrate layer, made from polyimide as disclosed previously, can be coated with reactive metals such as copper, aluminum, or chromium using commonly available techniques such as vapor deposition or sputtering. The coated substrate is then placed in a solution containing the isotope. The difference in oxidation-reduction (redox) potential between the coating metal and the isotope causes the isotope to deposit on the surface of the substrate film. This system can also be used to attach W-188 from a solution of tungsten salts or other metal salt isotopes as well.

In yet another system, the surface of the substrate 12 can be coated with a silver and/or silver halide layer such as Ag/AgI to further react with I-125. Metal isotope species, such as Palladium-103 (Pd-103) or Tungsten/Rhenium-188 (W/Re-188) or Gd-153 can be attached by incorporating a chelating agent onto the polymer substrate, and then soaking the sheet in a solution of Paladium salts, Tungsten salts or Gadolinium salts. These types of chemical technologies can be incorporated into the source design described herein.

There are alternative ways of taking advantage of the thin film structural properties, however, without utilizing a chemical attachment system for the isotopes. For example, the radioactive isotope can be attached directly to the sheet without a distinct tie layer 14 through a method known as Ion Implantation. Thus, for some techniques, a distinct tie layer 14 is omitted completely. See FIG. 1A. Ion Implantation systems are commercially available from companies such as IICO (Santa Clara, Calif.) and Varian (Menlo Park, Calif.), and most metals and semimetals (P, W, Pd, I, etc . . . ) can be implanted into the thin flexible substrate materials described earlier. With this technology, isotope layers of less than 1 micron are deposited on the substrate, thus the mechanical characteristics of the thin film are substantially the same as the chemical attachment version. Therefore, all of the physical/mechanical advantages described in the above paragraphs are maintained: flexibility, ability to adjust activity based on multiple wraps, ability to utilize less active isotopes.

Other methods of direct isotope attachment to the substrate can be considered for metal isotopes. For example, vapor deposition and sputtering can be used to deposit metal isotopes on the substrate. As with Ion Implantation, the metal layers can be controlled to submicron thicknesses, maintaining the mechanical characteristics achieved using Ion Implantation.

The source balloon preferably comprises thin film source mounted over the balloon with a cover layer. Alternatively, the balloon can be coated directly with an isotope with an optional cover layer over the isotope. However, a cover layer (such as a plastic) may not be necessary for this balloon, since the sheath catheter protects the patient from loose isotope particulate hazard.

In one embodiment, the source balloon is ion implanted or sputtered with silver ion. The silver is converted to AgCl in a solution of HCl and $NaClO_2$. The balloon is then dipped into a solution of Na125I, and the I-125 exchanges with the Cl and deposits on the balloon surface. This procedure produces a gamma emitting source in the 30 keV range, with a half life of about 60 days.

Alternatively, the source balloon can be ion implanted with Al and oxidized in $H_2O_2$ to form $Al_2O_3$ on the surface of the balloon. This is then dipped in a solution of $NaWO_4$. The WO4 ion binds to the $Al_2O_3$. This procedure produces a beta emitting source as the W-188 decays to Re-188, with energies in the 2.1 MeV range and a half like of about 70 days.

The dual catheter radiation delivery system of the present invention may be used as follows. First, a site in a vessel to be treated is identified. The site may be the site of a stenosis which requires dilatation or the site where a stenosis has previously been dilated, or a site within a previously implanted tubular prosthesis such as a stent or a graft. An expandable sheath balloon is percutaneously inserted and transluminally advanced through the patient's vasculature to position the sheath balloon at the selected site. A radiation delivery catheter having an expandable delivery balloon with a radiation delivery source thereon is advanced through the sheath catheter until the radiation delivery source is positioned within the expandable sheath balloon. At least the delivery balloon, and, preferably, both the delivery balloon and the sheath balloon are inflated such as with $CO_2$, to bring the radiation delivery source adjacent the interior wall of the sheath balloon. The radiation delivery balloon remains inflated for a sufficient radiation delivery period, and is thereafter deflated and withdrawn.

The radiation source may be secured to the radiation delivery balloon in any of a variety of manners, such as by ion implantation into the material of the radiation delivery balloon, chemical attachment to the radiation balloon, or by attachment of a thin film radiation source to the outside or inside of the radiation delivery balloon. The radioactive isotope contained in the radiation source may be bonded to or implanted within the thin film source.

The sheath balloon may be utilized to dilate a stenosis at the treatment site, prior to introduction of the radiation delivery balloon into the sheath balloon. Alternatively, the sheath balloon can be utilized to dilate a stenosis at the treatment site simultaneously with or following the delivery of radiation from the radiation delivery balloon while positioned within the sheath balloon.

In a further variation of the method of the present invention, an expandable tubular stent is positioned over the sheath balloon prior to positioning of the sheath balloon at the treatment site. The sheath balloon is expanded at the treatment site to expand the stent, which is left in position in the vessel following withdrawal of the dual catheter radiation delivery system from the patient. The stent can be expanded previous to, simultaneously with, or following the step of delivery a dose of radiation to the treatment site.

Although the present invention has been described in terms of certain preferred embodiments, other embodiments will become apparent to those of ordinary skill in the art in view of the disclosure herein. Accordingly, the present invention is not intended to be limited by the foregoing detailed description, but only by reference to the attached claims and drawings.

What is claimed is:

1. A radiation delivery system, comprising:

a sheath catheter, having proximal and distal ends;

a first inflatable balloon on a distal end of the sheath catheter, wherein said first balloon does not include a radiation source;

at least one lumen extending through the sheath catheter from the proximal end and communicating with the first balloon; and a source catheter axially movably positionable in the lumen, and having a radiation source thereon, wherein the radiation source is moveable from a first position having a reduced cross-sectional profile to facilitate advancement through the lumen to a second position having an enlarged cross-sectional profile.

2. A radiation delivery system as in claim 1, wherein the radiation source is positionable adjacent an interior surface of the first balloon when the first balloon is inflated.

3. A radiation delivery system as in claim 1, further comprising a tubular sleeve positioned concentrically around the radiation source.

4. A radiation delivery system as in claim 1, wherein the source catheter comprises a second inflatable balloon near a distal end thereof.

5. A radiation delivery system as in claim 4, wherein the radiation source is chemically attached to the second balloon.

6. A radiation delivery system as in claim 4, wherein the radiation source is ion implanted into the material of the second balloon.

7. A radiation delivery system as in claim 4, wherein the radiation source is attached to an outer wall of the second balloon.

8. A radiation delivery system as in claim 7, wherein the radiation source comprises a thin film source attached to an outside surface of the second balloon.

9. A radiation delivery system for delivering a dose of radiation to a site in a mammal, comprising:

an elongate flexible tubular body, having proximal and distal ends;

a first balloon having proximal and distal ends on a distal portion of the tubular body, wherein the distal end of the tubular body is spaced proximally apart from the distal end of the balloon, and said first balloon does not include a radiation source;

at least one lumen extending through the tubular body and communicating with the balloon; and a radiation source carried on a second inflatable balloon, said second inflatable balloon advanceable through the lumen.

* * * * *